US00PP11162P

United States Patent [19]

Utecht

[11] Patent Number: Plant 11,162

[45] Date of Patent: Dec. 21, 1999

[54] GERANIUM PLANT NAMED 'FISLYPSO'

[75] Inventor: Angelika Utecht, Montabaur, Germany

[73] Assignee: Florfis AG, Binningen, Switzerland

[21] Appl. No.: 08/968,045

[22] Filed: Nov. 12, 1997

[51] Int. Cl.[6] ..... A01H 5/00

[52] U.S. Cl. ..... Plt./329

[58] Field of Search ..... Plt./87.12, 329, Plt./324, 328

[56] References Cited

U.S. PATENT DOCUMENTS

P.P. 9,216 7/1995 Klemm ..... Plt./87.12

P.P. 9,217 7/1995 Trees ..... Plt./87.12

P.P. 9,970 7/1997 Hofmann ..... Plt./87.12

*Primary Examiner*—Howard J. Locker

*Attorney, Agent, or Firm*—Foley & Lardner

[57] ABSTRACT

A new distinct cultivar of geranium plant named 'Fislypso', particularly characterized by the combined features of violet flowers, umbrella-shaped umbels borne well above the foliage, uniform green foliage with weak zonation, early to medium flower response, and its wide but relatively low growth habit.

1 Drawing Sheet

The present invention comprises a new and distinct cultivar of geranium, botanically known as *Pelargonium zonale,* and referred to by the cultivar name 'Fislypso'.

'Fislypso' is a product of a planned breeding program which had the objective of creating an improved zonal geranium cultivar with light violet semi-double flowers in combination with intense green foliage.

'Fislypso' was originated from a hybridization made by the inventor Angelika Utecht in a controlled breeding program in Galdar, Gran Canaria, Spain in 1992. The female parent was the purple pink colored cultivar 'Penve'(U.S. Plant Pat. No. 9,970) having 6–7 petals per flower, light to medium green foliage with weak zonation, compact plant habit with inflorescences well above the foliage, and early flowering. The male parent of 'Fislypso' was 'Fischiro' (unpatented), characterized by single, light violet flowers, dark green foliage without or with only very weak zonation, and compact plant habit.

'Fislypso' was selected as one flowering plant within the progeny of the stated cross by Angelika Utecht in 1993 in a controlled environment in Galdar, Gran Canaria, Spain.

The first act of asexual reproduction of 'Fislypso' was accomplished when vegetative cuttings were taken from the initial selection in Autumn 1993 in a controlled environment in Galdar, Gran Canaria, Spain, by, or under the supervision of, Angelika Utecht.

Horticultural examination of plants grown from these cuttings initiated in May, 1994 in Hillscheid, Federal Republic of Germany, and continuing thereafter, has demonstrated that the combination of characteristics as herein disclosed for 'Fislypso', are firmly fixed and are retained through successive generations of asexual reproduction.

'Fislypso', has not been observed under all possible environmental conditions. The phenotype may vary significantly with variations in environment such as temperature, light intensity and daylength, without, however, any variation in genotype.

The following observations, measurements, and comparisons describe plants grown in Hillscheid, Federal Republic of Germany, under greenhouse conditions which approximate those generally used in commercial practice.

The following traits have been repeatedly observed and are determined to be basic characteristics of 'Fislypso', which in combination distinguish this geranium as a new and distinct cultivar:

1. Violet colored flowers with small white eyes.
2. 6–7 petals per flower, open flower shape.
3. Uniform, light to medium green foliage with weak zonation.
4. Medium vigorous growth, wide but relatively low plant habit.
5. Umbrella-shaped inflorescences well above the foliage.
6. Medium to early spring flowering response.

Of the many commercial cultivars known to the present inventor, the most similar in comparison to 'Fislypso' is the parent cultivar 'Penve'. In comparison to 'Penve', 'Fislypso' has similarly shaped flowers but with a distinctly more bluish hue of flower color, and longer peduncles. In addition, 'Fislypso' grows more vigorously, develops larger leaves, and does not begin to flower quite as early as 'Penve'.

The accompanying photographic drawing shows typical flower and foliage characteristics of 'Fislypso', with colors being as true as possible with illustrations of this type.

In the following description, color references are made to The Royal Horticultural Society Color Chart. The color values were determined indoors in from flowers taken from plants grown in a greenhouse in May 1995 in Hillscheid, Germany.

Classification:

*Botanical.*—A hybrid of the species *Pelargonium zonale l'Hert.*

*Commercial.*—Zonal geranium, cv. 'Fislypso'.

Inflorescence:

*Umbel.*—Shape: Flat semi-spherical. Average diameter: 103 mm. Average depth: 52 mm. Peduncle length: 185 mm. Peduncle color: Mainly green, R.H.S. 144 A–B, often reddish on the side well exposed to the light, about R.H.S. 179 B. Pedicel length: 24 mm. Pedicel color: Main color R.H.S. 144 C (light green), upper third R.H.S. 181 A (brown red). Number of flowers per umbel: about 25–45.

*Corolla.*—Average diameter: 44 mm. Shape: Almost round, open. Number of petals: Most often 6–7. Number of petaloids: 2–4. Color (general tonality from a distance of three meters): Violet. Color of upper petals: 78 B. Markings, of upper petals: White eyes at the base of the upper petals are R.H.S. 155 D to R.H.S. 75 D with fine pink veins. Color of lower petals: 78 B. Color of lower surface of petals: 78 C, lower side with distinct purple veins, R.H.S. 67 A. Color of sepals: Mainly light green, base red. Number of sepals: 5.

*Bud.*—Shape: Elliptical. Size: just before unfolding, approximately 18 mm in length and 10 mm in width. Color (adaxial): Light green, R.H.S 144B. Color (abaxial): Violet pink, somewhat variable between R.H.S. 74 D–R.H.S. 78 D.

*Reproductive organs.*—Androecium: 3–5 fertile anthers; pink and white filaments, yellow-orange pollen. Gynoecium: 5–6 lobed stigma, purple with pink filament. Fertility/seed set: A few seeds may occur in late Summer or Autumn

*Spring flowering response period.*—In Hillscheid, Germany, in 1995 plants had on average 0.9 flowers opened 11 weeks after planting of unrooted cuttings.

*Outdoor flower production.*—The flower count in 1994 in Hillscheid, Germany indicated about 35 inflorescences per plant for May through August observation period.

*Durability.*—Good shatter resistance, relatively good rain resistance.

Plant:

*Foliage.*—Form: Kidney-shaped. Margin: Bicrenated. Size of leaf: 95 mm. Color of upper surface: Light to medium green, approximately 137 D. Color of under surface: between R.H.S. 144 D and 143 C. Color of zonation: Dark green or slightly brownish, R.H.S. 147 A, may fade during the summer months. Tolerance of botrytis: Average.

*General appearance and form.*—Internode length: 5–15 mm. Branching pattern: 5.0 branches, 12-week-old plants. Height of plants: 25 cm (in September, based on 35-week old plants).

I claim:

1. A new and distinct cultivar of geranium plant named 'Fislypso', as described and illustrated.

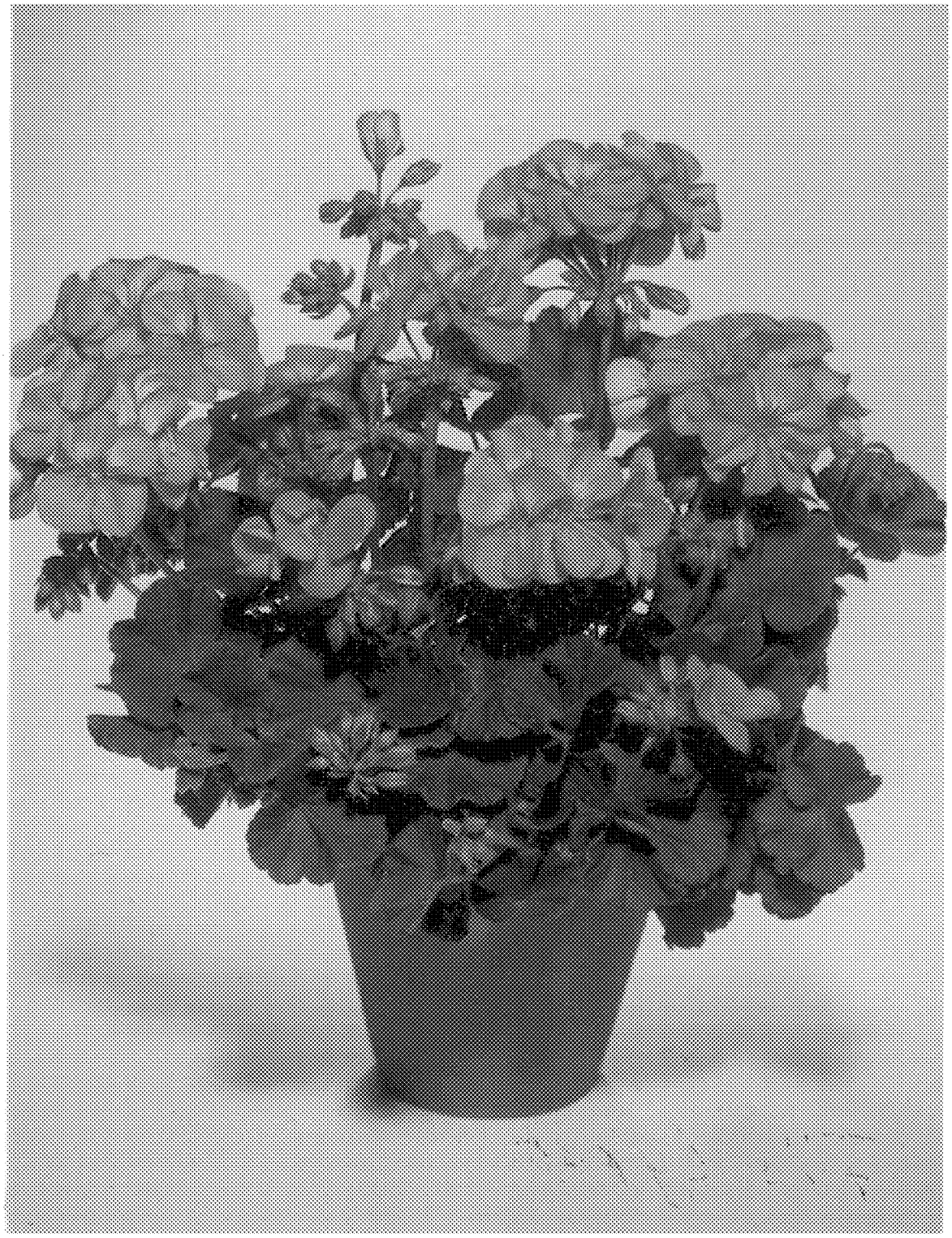

* * * * *